US00PP28323P3

(12) United States Plant Patent
Suphachadiwong

(10) Patent No.: US PP28,323 P3
(45) Date of Patent: Aug. 22, 2017

(54) *VANDA* PLANT NAMED 'SPCDW1407'

(50) Latin Name: ***Vanda* spp. Jones ex R. Br.**
Varietal Denomination: SPCDW1407

(71) Applicant: Thumrong Suphachadiwong, Bangphra (TH)

(72) Inventor: Thumrong Suphachadiwong, Bangphra (TH)

(73) Assignee: Suphatchatwong Innovation Co., Ltd., Bangphra (TH)

( * ) Notice: Subject to any disclaimer, the term of this patent is extended or adjusted under 35 U.S.C. 154(b) by 61 days.

(21) Appl. No.: 14/757,063

(22) Filed: Nov. 13, 2015

(65) Prior Publication Data

US 2016/0143204 P1 May 19, 2016

(30) Foreign Application Priority Data

Nov. 14, 2014 (QZ) ..... PBR 2014/2942

(51) Int. Cl.
*A01H 5/02* (2006.01)

(52) U.S. Cl.
USPC ..... Plt./311

(58) Field of Classification Search
USPC ..... Plt./311
See application file for complete search history.

*Primary Examiner* — June Hwu
(74) *Attorney, Agent, or Firm* — Samuel R. McCoy, Jr.

(57) ABSTRACT

A new and distinct *Vanda* cultivar named 'SPCDW1407' which is characterized by the combination of sepals and petals with a unique light pink color, contrasted against a lighter pink to white background color, unique fine tessellated patterning of the sepals and petals, a dark pink labellum, frequent flowering, vigorous growth, and the stability of all characteristics from generation to generation. The new variety is a *Vanda,* typically produced as an indoor ornamental plant.

3 Drawing Sheets

Latin name of the genus and species: The Latin name of the genus and species of the novel variety disclosed herein is *Vanda* Jones ex R. Br.

Variety denomination: The inventive variety of *Vanda* disclosed herein has been given the variety denomination 'SPCDW1407'.

CROSS REFERENCE TO RELATED APPLICATIONS

This application claims priority to the Community Plant Variety Rights application number 2014/2942, filed Nov. 14, 2014, which is herein incorporated by reference.

BACKGROUND OF THE INVENTION

Parentage: The *Vanda* variety 'SPCDW1407' is the result of a planned breeding program. The new variety originated as a seedling from the crossing of the unpatented, proprietary seed parent *Vanda* '02PBP' with the unpatented, proprietary pollen parent *Vanda* 'KMK84'. Both parents were developed by, and are owned by, the inventor and were never commercially released. The crossing was made by the inventor in his research greenhouse in Bangphra, Thailand in October of 2002.

The new variety was first selected in April of 2007, in a research greenhouse in Bangphra, Thailand belonging to the inventor. After identifying the new variety as a potentially interesting selection, the inventor continued confidential testing and propagation of 'SPCDW1407', assessing stability of the unique characteristics of this variety.

Asexual Reproduction: Asexual reproduction of the new cultivar 'SPCDW1407', by way of mericloning, was first initiated in April of 2009 at a commercial laboratory belonging to the inventor in Bangphra, Thailand, with the first mericlones so reproduced flowering in 2014. Access to all plants was restricted, as plants were kept in a greenhouse not open to the public, and tissue culture plantlets were in a laboratory belonging to the inventor, and not accessible to the public. Through five subsequent generations, the unique features of this cultivar have proven to be stable and true to type.

SUMMARY OF THE INVENTION

The cultivar 'SPCDW1407' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1407'. These characteristics in combination distinguish 'SPCDW1407' as a new and distinct *Vanda* cultivar:

1. *Vanda* 'SPCDW1407' exhibits sepals and petals with a unique light pink color, contrasted against a lighter pink to white background color, in combination with unique fine tessellated patterns of the sepals and petals; and
2. *Vanda* 'SPCDW1407' exhibits a dark pink general tonality of the labellum; and
3. *Vanda* 'SPCDW1407' is very vigorous and easy to produce; and
4. *Vanda* 'SPCDW1407' flowers frequently.

BOTANICAL DESCRIPTION OF THE PLANT

Figure 1:
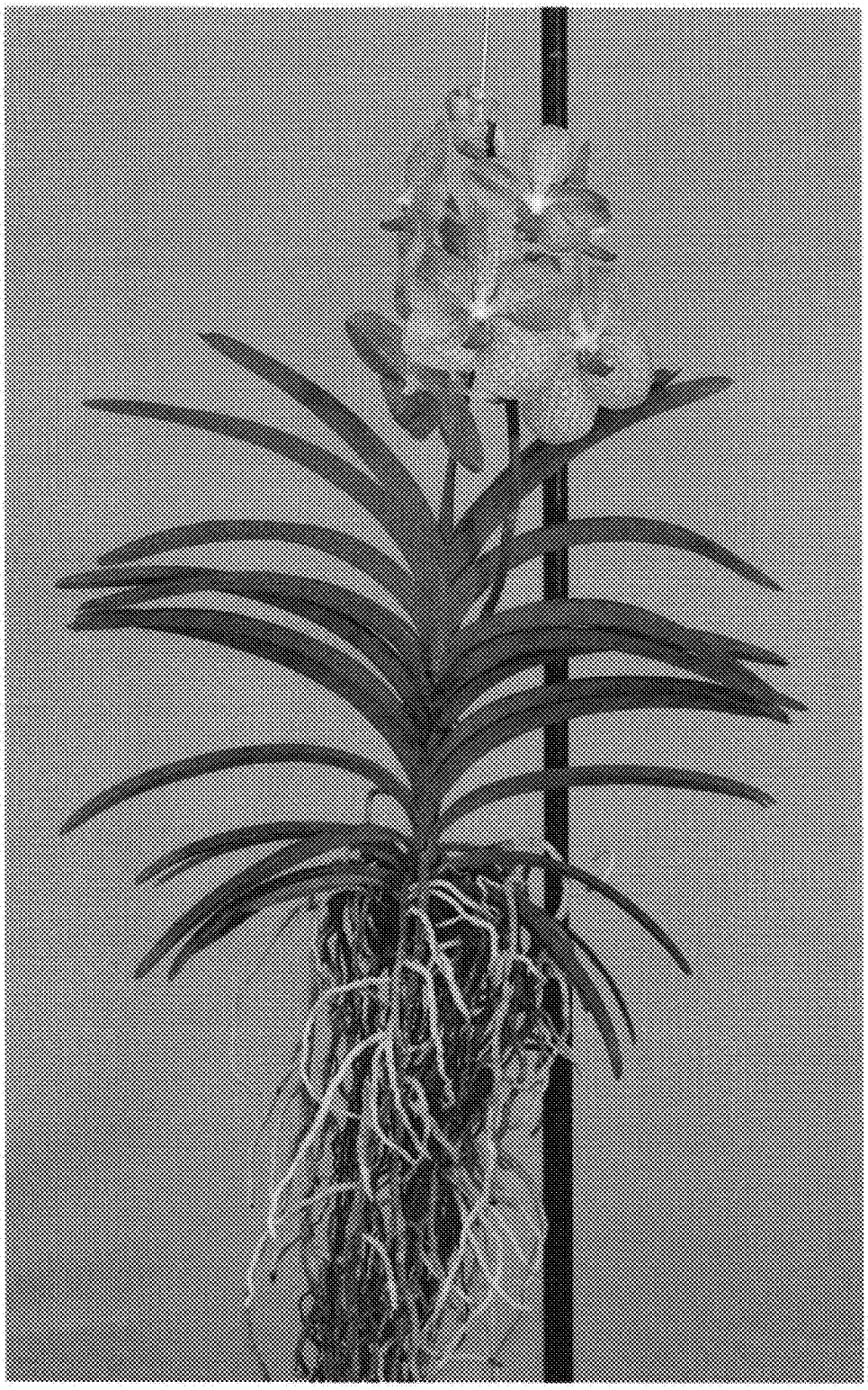
FIG. 1 illustrates, as nearly true as it is reasonably possible to make the same in color photographs of this type, an exemplary plant of 'SPCDW1407' grown in a commercial greenhouse in Honselersdijk, the Netherlands. This plant is approximately 6 years old from the time of mericloning, shown planted in an 8 by 8 cm container.
Figure 2:
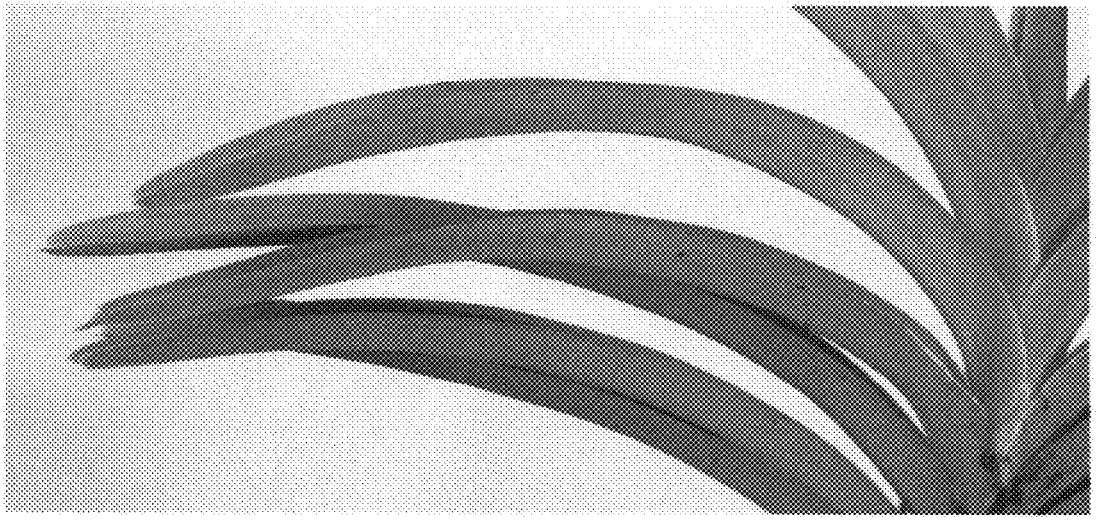
FIG. 2 illustrates, as nearly true as it is reasonably possible to make the same in color photographs of this type, the typical foliage of 'SPCDW1407'.
Figure 3:
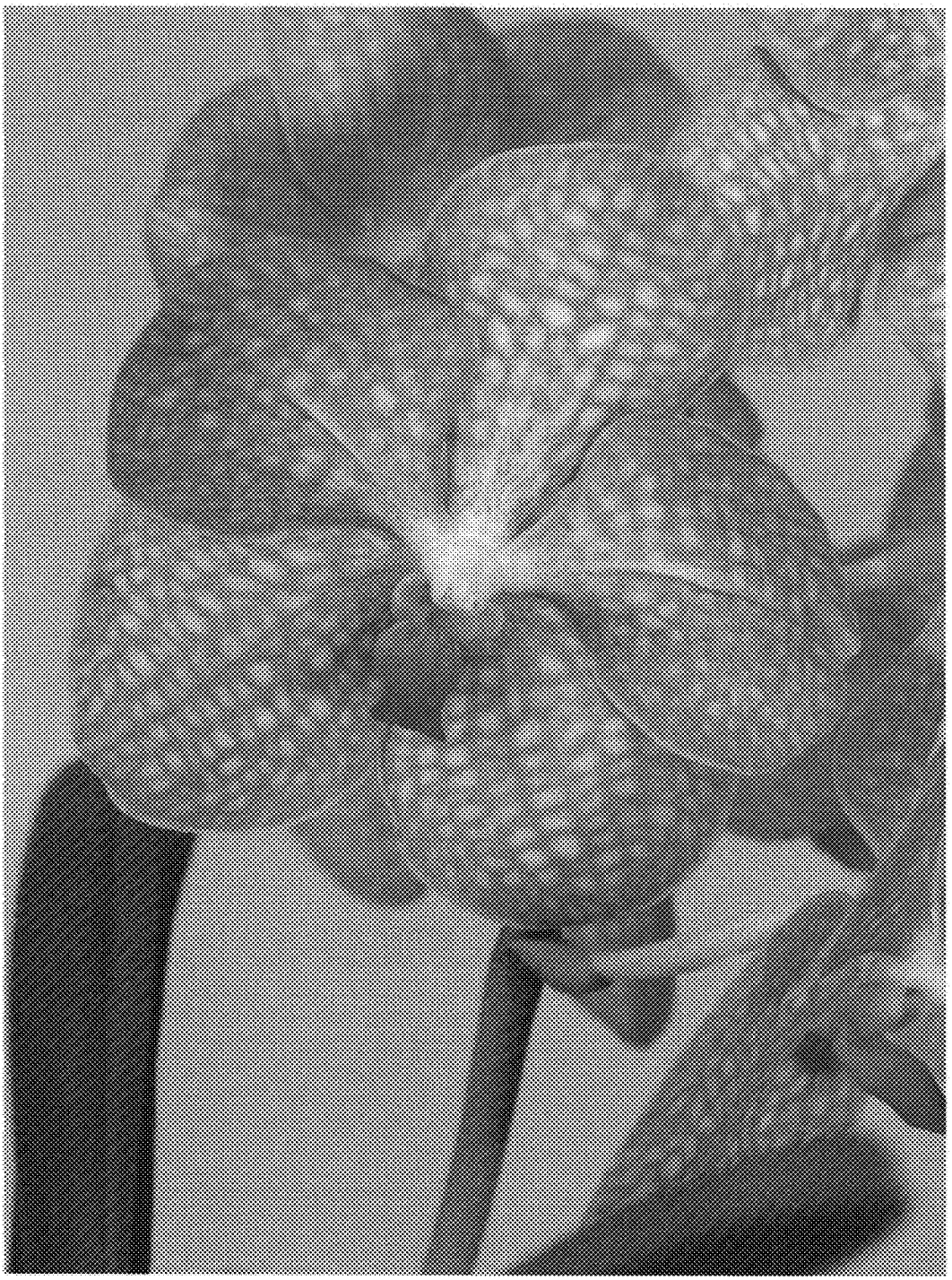
FIG. 3 illustrates, as nearly true as it is reasonably possible to make the same in color photographs of this type, the typical flowers of 'SPCDW1407'.

The following observations and measurements made in October of 2015 describe averages from a sample set of six specimens of six year-old 'SPCDW1407' plants grown in a greenhouse in Honselersdijk, the Netherlands. Temperatures ranged were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1407' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart,* The Royal Horticultural Society, London, 2015 (sixth edition).

A botanical description of 'SPCDW1407' and comparisons with other varieties of *Vanda* are provided below.

Plant description:

- *Growth habit.*—Perennial; monopodial, upright. Single monopodial leafy stem, with flowers carried slightly above the leaf plane, inflorescences grow from the leaf axils.
- *Average height from base (plant grown in hanging basket, so no soil line present) to top of foliage.*—39.2 cm.
- *Average height from base (plant grown in hanging basket, so no soil line present) to top of flowers.*—55.6 cm.
- *Plant spread.*—Average of 46.8 cm.
- *Normal pot size.*—Hanging basket (8 by 8 cm, square).
- *Growth rate.*—Moderate.
- *Plant vigor.*—Moderate.
- *Propagation type.*—Tissue culture propagation using the base of the leaves.
- *Propagation details.*—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.
- *Disease and pest resistance or susceptibility.*—Similar to other *Vanda* varieties.
- *Environmental tolerances.*—Adapt to, at least, USDA Zones 11 and 12; high tolerance to rain; moderate to high tolerance to wind.

Root system:

- *General.*—Densely rooting; with aerial roots only.
- *Dimensions, mature roots.*—55.5 cm long with a diameter of 0.6 cm, on average.
- *Texture.*—Very fleshy; non-fibrous.
- *Color.*—Greyed-Green, near RHS 192C to 192D; root apex is yellow-green, RHS 152A.

Stem:

- *Branching habit.*—Single monopodial leafy stem.
- *Number of primary (main) stems per plant.*—One.
- *Number of secondary (lateral) branches per plant.*—None.
- *Appearance and shape.*—Circular, formed by the leaf sheaths.
- *Length.*—23.5 cm.
- *Diameter.*—1.0 cm.
- *Internode length.*—0.6 cm.
- *Luster.*—Matte.
- *Aspect.*—Near vertical.
- *Strength.*—Very strong.
- *Color, juvenile.*—Yellow-green, near 150C to 150D.
- *Color, mature.*—Yellow-green, near 150C to 150D.
- *Color at internodes.*—Yellow-green, near 150C to 150D.
- *Pubescence.*—Glabrous.

Foliage:

- *Arrangement.*—Distichous.
- *Quantity.*—Approximately 26 leaves per plant.
- *Dimensions.*—23.6 cm long and 2.4 cm wide, on average.
- *Shape of blade.*—Ligulate; strongly carinate.
- *Aspect.*—Moderately curved.
- *Apex.*—Unequal praemorse.
- *Base.*—Sheathing.
- *Sheath dimensions.*—1.8 cm long and 1.4 cm wide, on average.
- *Sheath color.*—Yellow-Green, near RHS 144B.
- *Margin.*—Entire.
- *Pubescence, texture and luster of adaxial surface.*—Glabrous, smooth, and slightly glossy.
- *Pubescence, texture and luster of abaxial surface.*—Glabrous, smooth, and matte.
- *Color.*—Juvenile foliage, adaxial surface — Yellow-green, near RHS 144A to 144B. Juvenile foliage, abaxial surface — Yellow-green, near RHS 144A. Mature foliage, adaxial surface — Green to yellow-green, near in between RHS 143A and 146A. Mature foliage, abaxial surface — Yellow-green RHS 144A to 144B.
- *Venation.*—Parallel.
- *Venation color, adaxial surface.*—Green to yellow-green, near in between RHS 143A and 146A.
- *Venation color, abaxial surface.*—Yellow-green RHS 144B.
- *Petiole.*—No petioles present, leaves sessile.

Inflorescence:

- *Inflorescence arrangement.*—Axially placed raceme.
- *Natural flowering season.*—Autumn into winter.
- *Inflorescence quantity.*—One.
- *Flowers per inflorescence.*—Average of 7 open flowers and 4 unopened flower buds.
- *Inflorescence height.*—Approximately 22.0 cm (measured from base of lowest flower to top of upper flower).
- *Inflorescence diameter.*—Approximately 17.4 cm.

*Peduncle.*—Dimensions — Approximately 34.3 cm long and 0.6 cm wide. Aspect — Approximately 30° angle to lateral branch axis. Strength — Moderately strong. Texture and luster — Glabrous and moderately glossy. Color — Yellow-green, near RHS 144C.

Bud:

*Length.*—Average of 1.4 cm.

*Diameter.*—Average of 1.4 cm.

*Shape.*—Near globular.

*Pubescence, texture and luster.*—Glabrous, smooth and moderately glossy.

*Color.*—Yellow-green, near RHS 145C; apex and immature spur are tinged with purple, near N77D.

Flower:

*Flower type.*—Zygomorphic (orchidaceous), typical shape for the genus *Vanda*.

*Flowering habit.*—Moderate.

*Shape.*—Zygomorphic, single; consisting of three sepals and three petals, one of which is transformed into a labellum; the two lateral petals moderately overlap the dorsal sepal and the lateral sepals; lateral sepals are touching; dorsal sepal is free of the lateral sepals.

*Aspect.*—Flowers are outward-facing to slightly nodding.

*Height.*—Approximately 11.1 cm.

*Diameter.*—Approximately 11.0 cm.

*Depth.*—Approximately 3.8 cm.

*Fragrance.*—No fragrance.

*Lastingness.*—3 weeks.

*Persistent.*—Self-cleaning.

*Petals.*—Quantity of Petals — 3; two conventional petals and one labellum. Arrangement — One lateral petal on each side. Length — Approximately 5.3 cm. Width — Approximately 4.9 cm. Shape — Broad ovate. Apex — Obtuse. Base — Cuneate. Margin — Entire; moderately undulate. Pubescence, texture and luster of upper surface — Glabrous, velvety and matte. Pubescence, texture and luster of lower surface — Glabrous, velvety and matte. Color when opening, upper surface — White, near RHS NN155D; heavily dotted and marbled purple, RHS N75A. Color when opening, lower surface — White, near RHS NN155D; heavily dotted and marbled purple, RHS N75A and N75B. Color when fully opened, upper surface — White, near RHS NN155D; slightly tinged purple, RHS N87C; lightly dotted purple at the base, nearest to N78B. Color when fully opened, lower surface — White, near RHS NN155D; lightly dotted purple at the base, nearest to N78B. Fading, upper surface — Not fading. Fading, lower surface — Not fading. Venation color, fully opened, upper surface — Purple, near N78B. Venation color, fully opened, lower surface — Purple, near N78BC; slightly darker towards the margins and apex, RHS N78B.

*Labellum.*—Shape — Three-lobed; the shape of the lateral lobes is broad ovate and the aspect is involute; the central lobe is broad ovate to near rhombic and the aspect is revolute. Length — Central lobe — Approximately 2.1 cm. Lateral lobes — Approximately 1.0 cm. Width — Central lobe — Approximately 1.2 cm. Lateral lobes — Approximately 0.6 cm. Apex — Central lobe — Emarginate. Lateral lobe — Obtuse. Base — Central lobe — Cuneate. Lateral lobes — Cuneate. Margin — Entire; central lobe moderately undulate and lateral lobes not undulate. Texture and luster of upper surface — Central lobe — Glabrous, velvety, and matte. Lateral lobes — Glabrous, velvety, and matte. Texture and luster of lower surface — Central lobe — Glabrous, velvety, and matte. Lateral lobes — Glabrous, velvety, and matte. Color when opening, upper surface — Central lobe — Purple, near RHS N78A; lighter towards the base, RHS N78B. Lateral lobes — White, near RHS NN155C; heavily marbled purple, near RHS N78D, with a small yellow dot, near RHS 9C. Color when opening, lower surface — Central lobe — Purple, near RHS N78A; lighter towards the base, RHS N78B. Lateral lobes — Purple-violet, near RHS N80D. Color when fully opened, upper surface — Central lobe — Purple, near RHS N78A; lighter towards the base, RHS N78C. Lateral lobes — White, near RHS NN155C; heavily marbled purple, near RHS N78D, with a small yellow dot, near RHS 9C. Color when fully opened, lower surface — Central lobe — Purple, near RHS N78A; lighter towards the base, RHS N78D. Lateral lobes — Purple-violet, near RHS N80D. Fading, upper surface — Not fading. Fading, lower surface — Not fading. Venation color, fully opened, upper surface — Central lobe — Purple, near RHS 77C. Lateral lobes — White, near RHS NN155C; heavily marbled purple, near RHS N78D. Venation color, fully opened, lower surface — Central lobe — Purple, near RHS N78A; lighter towards the base, RHS N78D. Lateral lobes — White, near RHS NN155C; heavily marbled purple, near RHS N78D.

*Spurs.*—Quantity — Average of 1. Length — Approximately 0.9 cm. Diameter — Approximately 0.4 cm. Vertical height — Approximately 0.7 cm, at the base. Shape — Short triangular. Apex — Bluntly acute. Base — Broad Cuneate. Pubescence, texture and luster — Glabrous, smooth, and slightly glossy. Color — Purple RHS 76C.

*Sepals.*—Quantity — Average of 3 unfused sepals. Arrangement — One dorsal sepal and two lateral sepals. Length — Dorsal sepal — Approximately 5.5 cm. Lateral sepals — Approximately 6.0 cm. Width — Dorsal sepal — Approximately 4.6 cm. Lateral sepals — Approximately 5.5 cm. Shape — Dorsal sepal — Broad ovate. Lateral sepals — Broad ovate. Apex — Obtuse. Base — Cuneate. Margin — Entire and slightly undulate. Pubescence, texture and luster — Glabrous, velvety, and matte. Color when opening, upper surface — White, near RHS NN155D; heavily dotted and marbled with purple RHS N75A. Color when opening, lower surface — White, near RHS NN155D; heavily dotted and marbled with purple RHS N75A and N75B. Color when fully opened, upper surface — White, near RHS NN155D; slightly tinged with purple RHS N78C. Color when fully opened, lower surface — White, near RHS NN155D. Fading, upper surface — Not fading. Fading, lower surface — Not fading. Venation color, fully opened, upper surface — Dorsal sepal — Purple, near RHS N78B. Lateral sepal — Purple, near RHS N78B to N78C. Venation color, fully opened, lower surface — Dorsal sepal — Purple, near RHS N78C; slightly darker towards the margins and apex, RHS N78B. Lateral sepal — Purple, near RHS N78D; slightly darker towards the margins and apex, RHS N78C.

*Pedicels.*—Length — Approximately 5.6 cm. Diameter — Approximately 0.45 cm. Angle — Approximately 60° angle to peduncle axis. Strength — Moderate. Texture — Glabrous, axially angled with 5 "ribs", axially twisted (due to resupination). Luster — Glossy. Color — White, RHS NN155B; slightly tinged with purple RHS 76C.

*Bract.*—Quantity — One bract present at the base of each pedicel. Shape — Broad ovate to near reniform; folded around the base of the pedicel. Dimensions — Average of 1.6 cm long and 2.0 cm wide. Apex — Broad acute. Base — Broad Cuneate. Margins — Entire. Color, both surfaces — Yellow-green, in between near RHS 149A and 150D.

Reproductive organs:

*Column.*—Length — Approximately 0.6 cm. Diameter — Approximately 0.7 cm. Color — White RHS NN155B; upper surface is tinged purple, near RHS 77C and 77D.

*Ovary.*—Position — Inferior. Diameter — Approximately 0.2 cm. Color — White RHS NN155B.

*Pollinia color.*—Yellow-orange RHS 17A to 17B.

Seed and fruit: No fruit and seed production has been detected to date.

COMPARISONS WITH THE PARENT PLANTS

Plants of the new cultivar 'SPCDW1407' are similar to the seed parent, *Vanda* '02PBP', in most horticultural characteristics. However 'SPCDW1407' differs from the seed parent in the following characteristics:

1. The petals and sepals of 'SPCDW1407' exhibit a pink general tonality, whereas the flowers of '02PBP' exhibit a darker pink general tonality.
2. The tessellated color pattern on the sepals and petals of 'SPCDW1407' is very prominent, whereas '02PBP' lacks tessellation of the petals and sepals.
3. 'SPCDW1407' exhibits more flowers per inflorescence when compared to '02PBP'.

Plants of the new cultivar 'SPCDW1407' are similar to the pollen parent, *Vanda* 'KMK84', in most horticultural characteristics. However 'SPCDW1407' differs from the pollen parent in the following characteristics:

1. The flowers of 'SPCDW1407' exhibit a light pink general tonality, whereas the flowers of 'KMK84' exhibit a darker pink general tonality.
2. 'SPCDW1407' is more vigorous and easier to propagate and produce when compared to 'KMK84'.
3. 'SPCDW1407' blooms four to five times per year in Thailand, whereas 'KMK84' typically blooms only once per year in Thailand.

COMPARISON WITH THE MOST SIMILAR *VANDA* CULTIVAR KNOWN TO THE INVENTOR

'SPCDW1407' is similar in many horticultural characteristics to the commercial variety *Vanda* 'SPCDW1316' (unpatented in the United States; Community Plant Variety Rights grant number 40414). However 'SPCDW1407' differs from 'SPCDW1316' in the following characteristics:

1. The flowers of 'SPCDW1407' exhibit a light pink general tonality, whereas the flowers of 'SPCDW1316' exhibit a darker pink general tonality.
2. The tessellate color pattern on the sepals and petals of 'SPCDW1407' is very prominent, whereas the tessellation of 'SPCDW1316' is less prominent.
3. The lateral lobes of the labellum of 'SPCDW1407' exhibit a light pink general tonality, whereas the lateral lobes of 'SPCDW1316' exhibit a darker pink general tonality.

That which is claimed is:

1. A new and distinct variety of *Vanda* plant named 'SPCDW1407', substantially as described and illustrated herein.

* * * * *